US012657710B2

(12) United States Patent
Usuda

(10) Patent No.: US 12,657,710 B2
(45) Date of Patent: Jun. 16, 2026

(54) MEDICAL INFORMATION PROCESSING APPARATUS, ENDOSCOPE SYSTEM, MEDICAL INFORMATION PROCESSING METHOD, AND MEDICAL INFORMATION PROCESSING PROGRAM

(71) Applicant: FUJIFILM Corporation, Tokyo (JP)

(72) Inventor: Toshihiro Usuda, Kanagawa (JP)

(73) Assignee: FUJIFILM Corporation, Tokyo (JP)

(*) Notice: Subject to any disclaimer, the term of this patent is extended or adjusted under 35 U.S.C. 154(b) by 200 days.

(21) Appl. No.: 18/473,287

(22) Filed: Sep. 25, 2023

(65) Prior Publication Data

US 2024/0013389 A1 Jan. 11, 2024

Related U.S. Application Data

(63) Continuation of application No. PCT/JP2022/011842, filed on Mar. 16, 2022.

(30) Foreign Application Priority Data

Mar. 26, 2021 (JP) ................................. 2021-053974

(51) Int. Cl.
G06T 7/62 (2017.01)
A61B 90/30 (2016.01)
(Continued)

(52) U.S. Cl.
CPC .............. *G06T 7/0012* (2013.01); *G06T 7/62* (2017.01); *G06T 17/00* (2013.01); *G16H 30/20* (2018.01); *G06T 2207/10068* (2013.01)

(58) Field of Classification Search
CPC ......... G06T 7/0012; G06T 7/62; G06T 17/00; G06T 2207/10068; G06T 2207/30028;
(Continued)

(56) References Cited

U.S. PATENT DOCUMENTS

2015/0287192 A1 10/2015 Sasaki
2017/0100019 A1* 4/2017 Ikuma ................ A61B 1/00009
(Continued)

FOREIGN PATENT DOCUMENTS

JP 2014138691 7/2014
JP 2018522622 8/2018
(Continued)

OTHER PUBLICATIONS

"International Search Report (Form PCT/ISA/210) of PCT/JP2022/011842," mailed on Jun. 7, 2022, with English translation thereof, pp. 1-5.
(Continued)

*Primary Examiner* — Siamak Harandi
(74) *Attorney, Agent, or Firm* — JCIPRNET

(57) ABSTRACT

A medical information processing apparatus according to an aspect of the present invention is a medical information processing apparatus including a processor. The processor is configured to execute a spatial information acquisition process of sequentially acquiring pieces of spatial information of a lumen on the basis of endoscopic images sequentially acquired by an endoscope; an estimation process of estimating, on the basis of the pieces of spatial information sequentially acquired, at least one of a three-dimensional environment map of the lumen or a distal end position of the endoscope; a reference information acquisition process of acquiring reference information about a shape and/or an absolute size of the lumen; and a correction process of correcting, using the reference information, one or more of the spatial information, the three-dimensional environment map, and the distal end position of the endoscope.

18 Claims, 9 Drawing Sheets

(51) Int. Cl.
    *G06T 7/00*          (2017.01)
    *G06T 17/00*        (2006.01)
    *G16H 30/20*        (2018.01)

(58) Field of Classification Search
    CPC . G06T 2207/30092; G06T 7/55; G16H 30/20;
             G16H 30/40; G16H 40/63; A61B 90/30;
             A61B 2034/2048; A61B 1/000094; A61B
                 1/00194; A61B 5/1076; A61B 1/045;
             G06N 3/0464; G06N 3/09; G02B 23/24
    See application file for complete search history.

(56)                References Cited

U.S. PATENT DOCUMENTS

2018/0174311 A1    6/2018   Kluckner et al.
2018/0214006 A1*   8/2018   Akimoto ............ A61B 1/00194
2020/0029789 A1    1/2020   Hirakawa 2022/0095889 A1*   3/2022   Sato ................... A61B 1/00194

FOREIGN PATENT DOCUMENTS

| | | |
|---|---|---|
| JP | 2020014711 | 1/2020 |
| WO | 2017057330 | 4/2017 |
| WO | 2020070647 | 4/2020 |
| WO | 2020101431 | 5/2020 |
| WO | 2021014584 | 1/2021 |

OTHER PUBLICATIONS

"Written Opinion of the International Searching Authority (Form PCT/ISA/237) of PCT/JP2022/011842," mailed on Jun. 7, 2022, with English translation thereof, pp. 1-8.
"Notice of Reasons for Refusal of Japan Counterpart Application", issued on Oct. 30, 2025, with English translation thereof, p. 1-p. 12.

\* cited by examiner

FIG. 6A

| RECOGNITION TARGET | ACTUALLY MEASURED VALUE |
|---|---|
| DISTAL END OF TREATMENT TOOL | 1 cm |

FIG. 6B

| RECOGNITION TARGET | ACTUALLY MEASURED VALUE |
|---|---|
| DISTAL END OF BIOPSY FORCEPS | 1 cm |
| DISTAL END OF SNARE | 2 cm |
| DISTAL END OF CLIP | 1 cm |

MEDICAL INFORMATION PROCESSING APPARATUS, ENDOSCOPE SYSTEM, MEDICAL INFORMATION PROCESSING METHOD, AND MEDICAL INFORMATION PROCESSING PROGRAM

CROSS-REFERENCE TO RELATED APPLICATIONS

The present application is a Continuation of PCT International Application No. PCT/JP2022/011842 filed on Mar. 16, 2022 claiming priority under 35 U.S.C § 119(a) to Japanese Patent Application No. 2021-053974 filed on Mar. 26, 2021. Each of the above applications is hereby expressly incorporated by reference, in its entirety, into the present application.

BACKGROUND OF THE INVENTION

1. Field of the Invention

The present invention relates to a medical information processing apparatus, an endoscope system, a medical information processing method, and a medical information processing program, and particularly relates to a technique of processing spatial information of a lumen.

2. Description of the Related Art

In an examination of a lumen using an endoscope system (an endoscope apparatus), oversight is a problem in many cases, and the completeness of observation, that is, "whether the inside of the lumen is observed thoroughly", is important. To check the completeness of observation, it is effective to create a "depth map" of the inside of the lumen. In recent years, a technique of creating a depth map has been actively studied and used not only in the medical field but also for grasping the shape of a general structure or the like.

Regarding such a technique, for example, JP2018-522622A describes that a three-dimensional model of a target organ is generated from data acquired by using a laparoscope or an endoscope. JP2020-014711A describes that a depth image representing a distance from a viewpoint of a medical image to an inner wall of a tubular structure is created.

SUMMARY OF THE INVENTION

A depth map is used not only to check the completeness of observation but also for other purposes, such as creation of a diagnosis report, and thus it is preferable to create the depth map accurately. Regarding other medical information based on a depth map, it is preferable to acquire accurate information. However, the related art such as JP2018-522622A and JP2020-014711A mentioned above does not take such circumstances into consideration.

The present invention has been made in view of these circumstances, and an object of the present invention is to provide a medical information processing apparatus, an endoscope system, a medical information processing method, and a medical information processing program that are capable of acquiring accurate medical information.

To achieve the above-described object, a medical information processing apparatus according to a first aspect of the present invention is a medical information processing apparatus including a processor. The processor is configured to execute a spatial information acquisition process of sequentially acquiring pieces of spatial information of a lumen on the basis of endoscopic images sequentially acquired by an endoscope; an estimation process of estimating, on the basis of the pieces of spatial information sequentially acquired, at least one of a three-dimensional environment map of the lumen or a distal end position of the endoscope; a reference information acquisition process of acquiring reference information about a shape and/or an absolute size of the lumen; and a correction process of correcting, using the reference information, one or more of the spatial information, the three-dimensional environment map, and the distal end position of the endoscope.

In the first aspect, pieces of spatial information of a lumen are sequentially acquired (as time-series information), at least one of a three-dimensional environment map of the lumen or a distal end position of an endoscope is estimated from the acquired pieces of spatial information, and one or more of the spatial information, the three-dimensional environment map, and the distal end position of the endoscope is corrected by using reference information about a shape and/or an absolute size of the lumen. Thus, accurate medical information (the spatial information, the three-dimensional environment map, the distal end position of the endoscope) can be acquired.

In a medical information processing apparatus according to a second aspect, in the first aspect, the processor is configured to acquire the spatial information by using a plurality of endoscopic images that are different in imaging position. In the present invention, spatial information can be acquired by using one endoscopic image, but use of a plurality of endoscopic images that are different in imaging position in the second aspect makes it possible to acquire accurate spatial information. The position of the endoscope in the lumen changes as a user inserts or removes the endoscope into or from the subject, and thus "a plurality of endoscopic images that are different in imaging position" can be acquired by acquiring endoscopic images during a period in which insertion or removal is being performed.

In a medical information processing apparatus according to a third aspect, in the first or second aspect, the processor is configured to execute an estimated value acquisition process of acquiring, from the spatial information and/or the three-dimensional environment map, an estimated value to be compared with the reference information, and in the correction process, correct one or more of the spatial information, the three-dimensional environment map, and the distal end position of the endoscope to cause the estimated value to approach the reference information.

In a medical information processing apparatus according to a fourth aspect, in the third aspect, the processor is configured to, in the estimated value acquisition process, acquire the estimated value at a position designated in the lumen.

In a medical information processing apparatus according to a fifth aspect, in the fourth aspect, the processor is configured to, in the spatial information acquisition process, sequentially acquire the endoscopic images via the endoscope, and in the estimated value acquisition process, designate the position on the basis of the acquired endoscopic images.

In a medical information processing apparatus according to a sixth aspect, in any one of the first to fifth aspects, the processor is configured to, in the reference information acquisition process, acquire, as the reference information, a numerical value indicating a standard size of the lumen. In the sixth aspect, a numerical value obtained by statistically processing the actual size of the lumen (for example, an average value, an average value±standard deviation, or the like) can be used as the "standard size of the lumen".

In a medical information processing apparatus according to a seventh aspect, in any one of the first to sixth aspects, the processor is configured to, in the reference information acquisition process, acquire, as the reference information, a predetermined actually measured value (an actually measured value of the shape and/or absolute size of the lumen).

In a medical information processing apparatus according to an eighth aspect, in the seventh aspect, the processor is configured to, in the reference information acquisition process, acquire, as the actually measured value, a value calculated in advance on the basis of a medical image captured by a medical image capturing apparatus. In the eighth aspect, a value calculated in advance on the basis of a medical image captured by a medical image capturing apparatus, such as a computed tomography (CT) apparatus or a magnetic resonance imaging (MRI) apparatus, can be acquired as the "actually measured value".

In a medical information processing apparatus according to a ninth aspect, in the seventh or eighth aspect, the processor is configured to, in the reference information acquisition process, recognize a photographic subject in an endoscopic image acquired via the endoscope, and acquire the actually measured value on the basis of a result of the recognition.

In a medical information processing apparatus according to a tenth aspect, in the ninth aspect, the processor is configured to recognize, as the photographic subject, an object having a known size, and acquire, as the actually measured value, a size of the lumen at a location at which the photographic subject is present. According to the tenth aspect, the size of the lumen at the location at which the photographic subject is present can be accurately calculated through comparison with an object having a known size.

In a medical information processing apparatus according to an eleventh aspect, in the ninth or tenth aspect, the processor is configured to recognize, as the photographic subject, a tool protruding from the endoscope. According to the eleventh aspect, as a result of measuring the size of a tool such as a treatment tool in advance, the size can be used as an actually measured value in a case where the tool is recognized as a photographic subject in an endoscopic image.

In a medical information processing apparatus according to a twelfth aspect, in any one of the seventh to eleventh aspects, the processor is configured to, in the reference information acquisition process, acquire the actually measured value by using a measurement apparatus connected to the medical information processing apparatus. The measurement apparatus that acquires an actually measured value may be an apparatus that measures the shape and/or absolute size of a lumen by using laser or magnetism.

To achieve the above-described object, an endoscope system according to a thirteenth aspect of the present invention includes the medical information processing apparatus according to any one of the first to twelfth aspects; and an endoscope including an imaging unit configured to sequentially capture medical images of a subject. The endoscope system according to the thirteenth aspect includes the medical information processing apparatus according to any one of the first to twelfth aspects, and is thus capable of acquiring accurate medical information.

To achieve the above-described object, a medical information processing method according to a fourteenth aspect of the present invention is a medical information processing method to be executed by a medical information processing apparatus including a processor. The medical information processing method includes a spatial information acquisition step of sequentially acquiring pieces of spatial information of a lumen on the basis of endoscopic images sequentially acquired by an endoscope; an estimation step of estimating, on the basis of the pieces of spatial information sequentially acquired, at least one of a three-dimensional environment map of the lumen or a distal end position of the endoscope; a reference information acquisition step of acquiring reference information about a shape and/or an absolute size of the lumen; and a correction step of correcting, using the reference information, one or more of the spatial information, the three-dimensional environment map, and the distal end position of the endoscope. According to the fourteenth aspect, as in the first aspect, accurate medical information can be acquired. The medical information processing method according to the fourteenth aspect may further execute processes similar to those according to the second to twelfth aspects.

To achieve the above-described object, a medical information processing program according to a fifteenth aspect of the present invention is a medical information processing program that causes a medical information processing apparatus including a processor to execute a medical information processing method. The medical information processing method includes a spatial information acquisition step of sequentially acquiring pieces of spatial information of a lumen on the basis of endoscopic images sequentially acquired by an endoscope; an estimation step of estimating, on the basis of the pieces of spatial information sequentially acquired, at least one of a three-dimensional environment map of the lumen or a distal end position of the endoscope; a reference information acquisition step of acquiring reference information about a shape and/or an absolute size of the lumen; and a correction step of correcting, using the reference information, one or more of the spatial information, the three-dimensional environment map, and the distal end position of the endoscope. According to the fifteenth aspect, as in the first and fourteenth aspects, accurate medical information can be acquired. The medical information processing program according to the fifteenth aspect may cause processes similar to those according to the second to twelfth aspects to be further executed. A non-transitory recording medium storing a computer-readable code of the medical information processing program according to these aspects may be included in an aspect of the present invention.

As described above, the medical information processing apparatus, the endoscope system, the medical information processing method, and the medical information processing program according to the present invention are capable of acquiring accurate medical information.

BRIEF DESCRIPTION OF THE DRAWINGS

FIGS. 6A and 6B are tables illustrating examples of sizes (actually measured values) of treatment tools;

DESCRIPTION OF THE PREFERRED EMBODIMENTS

Hereinafter, a preferred embodiment of a medical information processing apparatus, an endoscope system, a medical information processing method, and a medical information processing program according to the present invention will be described with reference to the accompanying drawings.

Acquisition of Depth Information from Endoscopic Image

First, acquisition of depth information from an endoscopic image will be described.

Figure 1A:
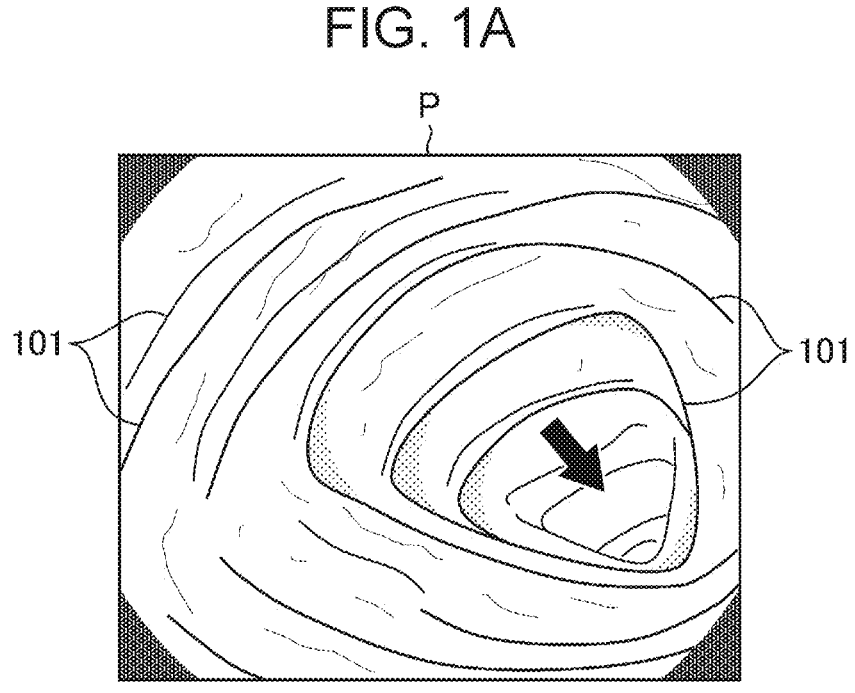
FIGS. 1A and 1B are diagrams schematically illustrating an endoscopic image and a depth image acquired from the endoscopic image.
Figure 1B:
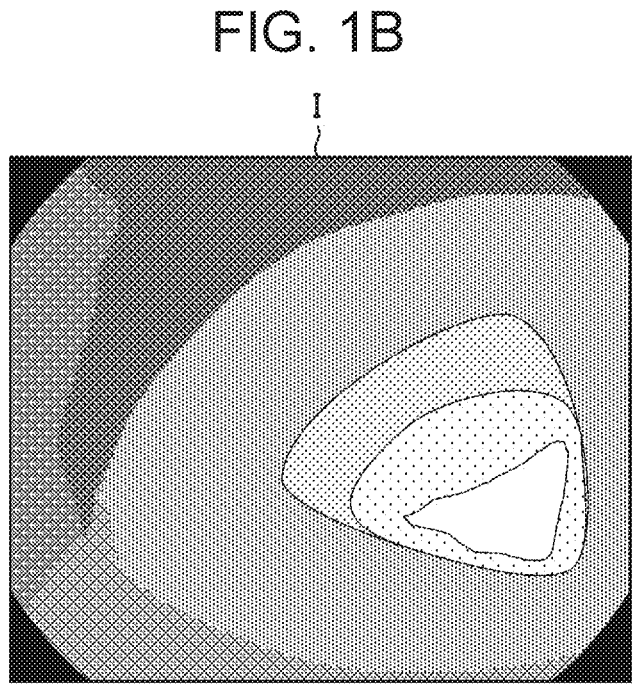

FIGS. 1A and 1B are diagrams schematically illustrating an endoscopic image and a depth image acquired from the endoscopic image.

Figure 3:
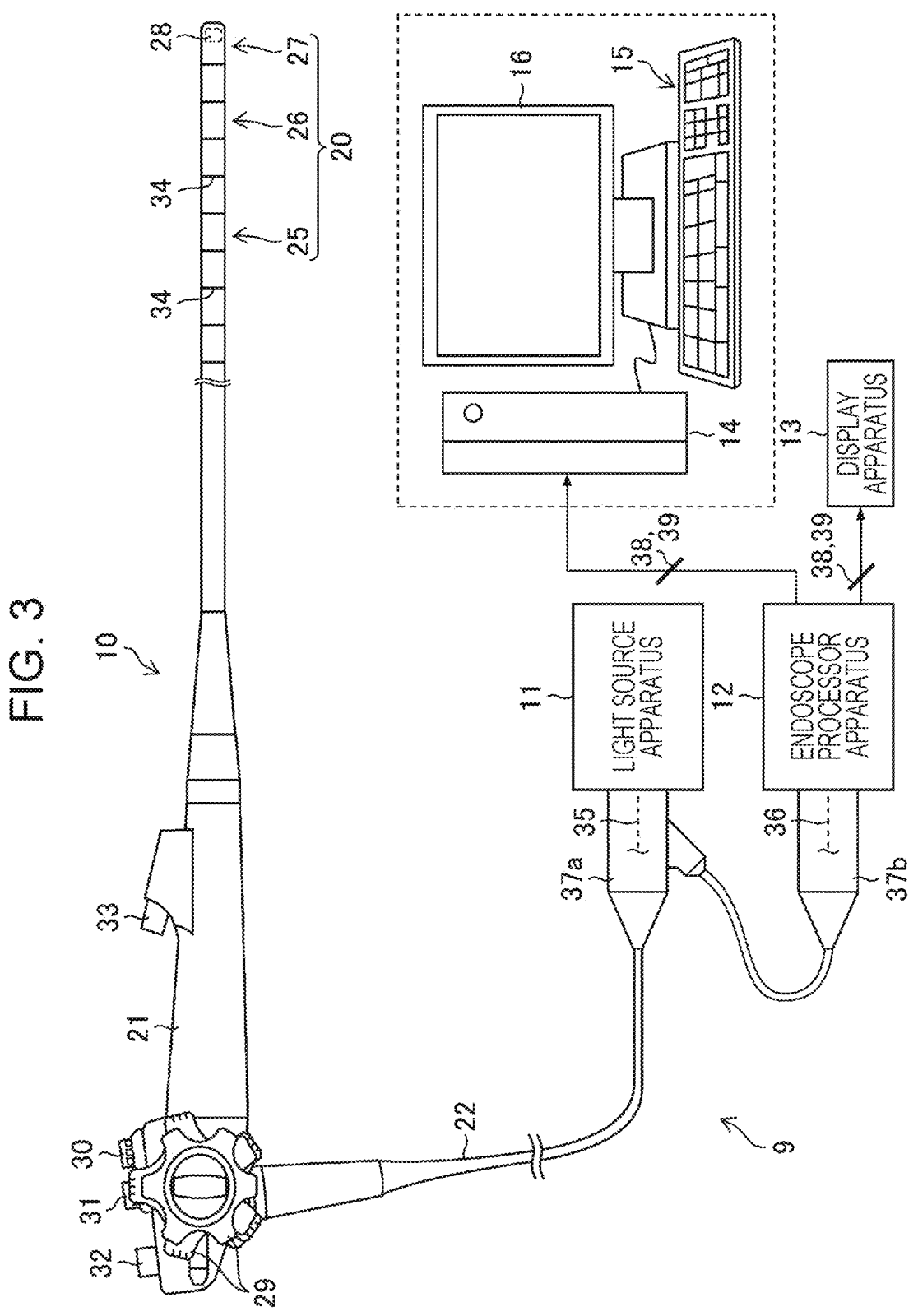
FIG. 3 is a schematic diagram illustrating an overall configuration of an endoscope system.

FIG. 1A illustrates an intraluminal image P (an endoscopic image), which is an example of an endoscopic image, acquired by an endoscope system 9 (an endoscope system; see FIG. 3). The intraluminal image P is, for example, an image of the inside of a large intestine. In the intraluminal image P, folds 101 in the large intestine are seen, and the lumen continues in the direction indicated by the arrow. On the other hand, a depth image I (spatial information of a lumen) illustrated in FIG. 1B is an image having depth information corresponding to the intraluminal image P. The depth image I has information about a depth (distance) from a camera (for example, a lens (not illustrated), an imaging element 28 or the like: an imaging unit). In the depth image I, depth information is indicated in a heat map manner (the color and the density thereof indicate the depth). The depth image I is illustrated in a simplified manner, and specifically has seven regions having respective pieces of depth information different from each other. In the depth image I, depth information may be actually indicated by more regions in a heat map manner, or different pieces of depth information may be indicated in units of pixels, for example. In this example, a description will be given of, as an example of an intraluminal image, an image of a large intestine observed by using the endoscope system 9, but the example of the intraluminal image is not limited thereto. The intraluminal image may be an image of another luminal organ. For example, in the case of an endoscope system for upper endoscopy, an esophagus, a stomach, or the like may be a luminal organ.

Normally, the above-described depth image I having depth information is acquired by using images of a plurality of viewpoints whose relative positional relationship is known, such as images acquired by a stereo camera. However, the endoscope system 9 includes a monocular camera (a lens (not illustrated), the imaging element 28 or the like; an imaging unit provided at a distal end part 27, see FIG. 3), and thus it is necessary to acquire depth information on the basis of an endoscopic image acquired by the monocular camera in the case of acquiring depth information.

For example, Daniel Freedman et al, "Detecting Deficient Coverage in Colonoscopies", CVPR2020, https://arxiv.org/pdf/2001.08589.pdf, describes a technique of acquiring a depth image having depth information from an endoscopic image acquired by a monocular camera by using a recognizer constituted by a convolutional neural network (CNN).

In the case of acquiring depth information by using only an endoscopic image captured by the above-described monocular camera, a relative depth is estimated by estimating the amount of movement of an endoscope 10 (see FIG. 3) between adjacent frames. In this case, because an organ is a non-rigid body, the lumen shape may be deformed in each frame, which may cause an error in depth information as described below.

Figure 2A:
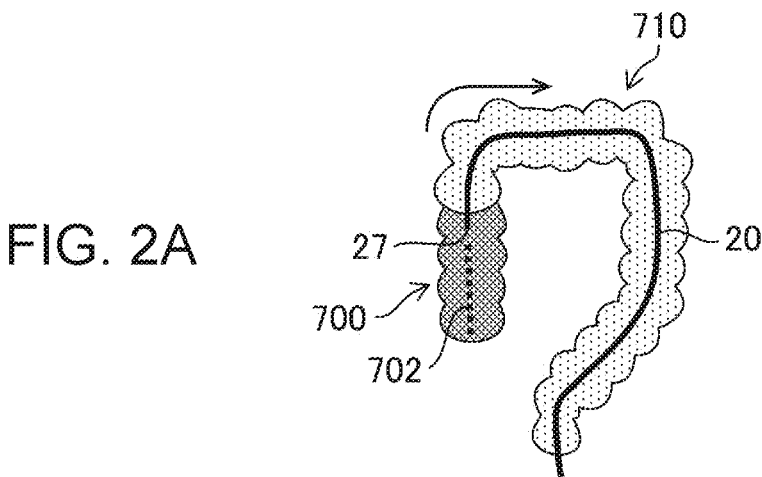
FIGS. 2A, 2B, and 2C are diagrams illustrating an influence of accumulated calculation errors on a depth map.
Figure 2B:
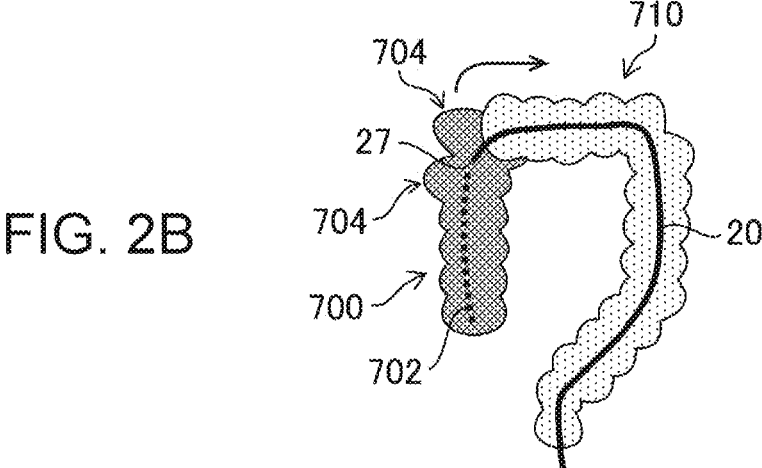
Figure 2C:
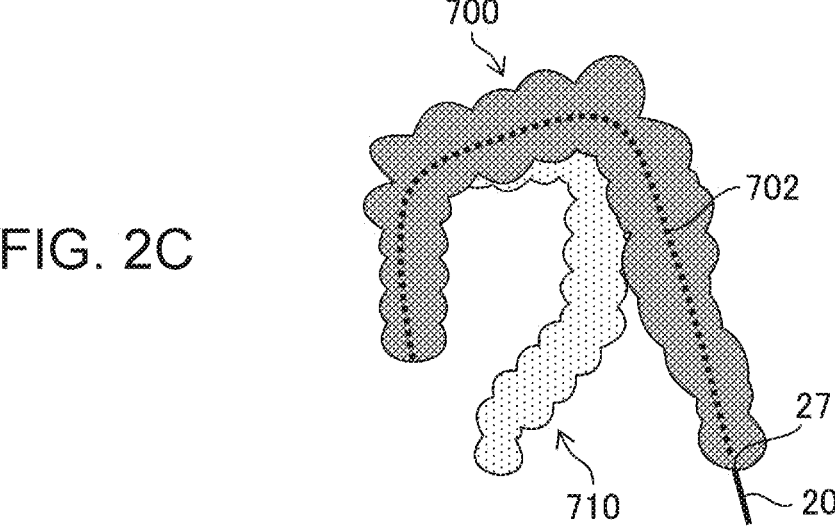

FIGS. 2A to 2C are diagrams illustrating an influence of accumulated calculation errors on a depth map (spatial information), and illustrate a state in which an insertion section 20 of the endoscope 10 is inserted into a large intestine. In this state, a user is able to perform observation while pulling out the insertion section 20 that has been inserted to the vicinity of the rectum. In accordance with the pulling-out operation, time-series endoscopic images (a plurality of endoscopic images that are different in imaging position) are acquired. In this case, as illustrated in FIG. 2A, the distal end part 27 moves in the direction indicated by the arrow. The trajectory of the insertion section is indicted by a dotted line 702. An example of an estimation result of spatial information in such a situation is a depth map 700 (a dark dotted region), and the actual shape of the large intestine corresponds to a large intestine 710 (a light dotted region).

FIG. 2B illustrates a state in which an estimation error occurs in a region 704 (the size is estimated to be larger than the actual size), and FIG. 2C illustrates a final estimation result. Estimation errors are accumulated in the depth map 700, causing large deviation from the actual shape and size of the large intestine 710. Such estimation errors occur, for example, because the lumen is handled as a rigid body.

As described above, it is preferable to acquire accurate information in consideration of, for example, checking of the completeness of observation. Accordingly, in the present invention, an estimated value of medical information (one or more of spatial information, a three-dimensional environment map, and a distal end position of an endoscope) is corrected by using reference information. Hereinafter, the details will be described.

First Embodiment

Overall Configuration of Endoscope System

FIG. 3 is a schematic diagram illustrating an overall configuration of an endoscope system. As illustrated in FIG. 3, the endoscope system 9 (an endoscope system) includes the endoscope 10 (an endoscope), which is an electronic endoscope, a light source apparatus 11, an endoscope processor apparatus 12, a display apparatus 13, a medical information processing apparatus 14 (a processor, a medical information processing apparatus), an operation unit 15, and a display unit 16.

The endoscope 10 captures time-series endoscopic images including an image of a photographic subject, and is, for example, a scope for a lower or upper digestive tract. The endoscope 10 has the insertion section 20 that is to be inserted into a subject (a lumen of a stomach, a large intestine, or the like) and that has a distal end and a base end, a handheld operation section 21 that communicates with the base end side of the insertion section 20 and that is to be grasped by a medical doctor as an operator to perform various operations, and a universal cord 22 that communicates with the handheld operation section 21.

The insertion section 20 is formed in an elongated shape with a small diameter as a whole. The insertion section 20 includes a soft part 25 having flexibility; a bending part 26 that is bendable by an operation of the handheld operation section 21; and the distal end part 27 in which an imaging optical system (an objective lens) that is not illustrated, the imaging element 28, and the like are built, which are disposed in this order from the base end side toward the distal end side of the insertion section 20. The insertion section 20 is marked with graduations 34 indicating the insertion length (amount of push) of the insertion section 20.

The imaging element 28 is an imaging element of a complementary metal oxide semiconductor (CMOS) type or a charge coupled device (CCD) type. Image light of an observed area is incident on the imaging surface of the imaging element 28 through an observation window that is not illustrated and that is opened in the distal end surface of the distal end part 27 and an objective lens that is not illustrated and that is disposed behind the observation window. The imaging element 28 captures image light of the observed area incident on the imaging surface (converts the image light into an electric signal) and outputs an imaging signal. That is, endoscopic images are sequentially captured by the imaging element 28. The endoscopic images are acquired as a moving image 38 and a still image 39, which will be described below.

The handheld operation section 21 is provided with operation members that are to be operated by a medical doctor (user). Specifically, the handheld operation section 21 is provided with two types of bending operation knobs 29 to be used for a bending operation of the bending part 26, an air/water supply button 30 for an air/water supply operation, and a suction button 31 for a suction operation. The handheld operation section 21 is also provided with a still image capturing instruction unit 32 for providing an instruction to capture the still image 39 of an observed area, and a treatment tool introduction port 33 for inserting a treatment tool (not illustrated) into a treatment tool insertion path (not illustrated) that extends through the inside of the insertion section 20.

The universal cord 22 is a connection cord for connecting the endoscope 10 to the light source apparatus 11. The universal cord 22 has therein a light guide 35, a signal cable 36, and a fluid tube (not illustrated) that extend through the inside of the insertion section 20. An end portion of the universal cord 22 is provided with a connector 37a that is connected to the light source apparatus 11 and a connector 37b that branches from the connector 37a and that is connected to the endoscope processor apparatus 12.

As a result of connecting the connector 37a to the light source apparatus 11, the light guide 35 and the fluid tube (not illustrated) are inserted into the light source apparatus 11. Accordingly, necessary illumination light, water, and air are supplied from the light source apparatus 11 to the endoscope 10 via the light guide 35 and the fluid tube (not illustrated). As a result, illumination light is radiated from an illumination window (not illustrated) on the distal end surface of the distal end part 27 toward the observed area. In response to a pressing operation of the above-described air/water supply button 30, air or water is ejected from an air/water supply nozzle (not illustrated) on the distal end surface of the distal end part 27 toward an observation window (not illustrated) on the distal end surface.

As a result of connecting the connector 37b to the endoscope processor apparatus 12, the signal cable 36 and the endoscope processor apparatus 12 are electrically connected to each other. Accordingly, an imaging signal of the observed area is output from the imaging element 28 of the endoscope 10 to the endoscope processor apparatus 12 (endoscopic images of the subject are sequentially captured at a predetermined frame rate), and a control signal is output from the endoscope processor apparatus 12 to the endoscope 10, through the signal cable 36.

The light source apparatus 11 supplies illumination light to the light guide 35 of the endoscope 10 via the connector 37a. As the illumination light, light in various wavelength ranges suitable for the purpose of observation, such as white light (light in a white wavelength range or light in a plurality of wavelength ranges; also referred to as normal light), light in one or a plurality of specific wavelength ranges (narrowband light or special light), or a combination thereof, is selected.

The endoscope processor apparatus 12 controls the operation of the endoscope 10 via the connector 37b and the signal cable 36. In addition, the endoscope processor apparatus 12 generates an image (also referred to as "moving image 38") constituted by time-series frame images 38a including a photographic subject image on the basis of an imaging signal acquired from the imaging element 28 of the endoscope 10 via the connector 37b and the signal cable 36. Furthermore, in response to the still image capturing instruction unit 32 being operated in the handheld operation section 21 of the endoscope 10, the endoscope processor apparatus 12 regards, in parallel with the generation of the moving image 38, one frame image 38a in the moving image 38 as the still image 39 that corresponds to the timing of the capturing instruction.

The moving image 38 and the still image 39 are endoscopic images obtained by capturing images of the inside of a subject, that is, the inside of a living body. Furthermore, in a case where the moving image 38 and the still image 39 are images obtained by using light in the above-described specific wavelength range (special light), both the images are special-light images. The endoscope processor apparatus 12 outputs the generated moving image 38 and still image 39 to the display apparatus 13 and the medical information processing apparatus 14.

The endoscope processor apparatus 12 may generate (acquire) the special-light image having information about the above-described specific wavelength range on the basis of the normal-light image acquired by using the above-described white light. In this case, the endoscope processor apparatus 12 functions as a special-light image acquisition unit. The endoscope processor apparatus 12 acquires a signal in the specific wavelength range by performing computation based on color information of red, green, and blue (RGB) or cyan, magenta, and yellow (CMY) included in the normal-light image.

In addition, the endoscope processor apparatus 12 may generate, for example, a feature quantity image, such as a known oxygen saturation image, on the basis of at least one of the normal-light image acquired by using the above-described white light or the special-light image acquired by using the above-described light in the specific wavelength range (special light). In this case, the endoscope processor apparatus 12 functions as a feature quantity image generation unit. The moving image 38 or the still image 39 including the above-described inside-of-living-body image, normal-light image, special-light image, and feature quantity image is an endoscopic image obtained by imaging a result of imaging or measuring a human body for the purpose of diagnosis or examination using an image.

The display apparatus 13 is connected to the endoscope processor apparatus 12 and functions as the display unit 16 that displays the moving image 38 and the still image 39 input from the endoscope processor apparatus 12. A medical doctor (user) performs an operation of moving the insertion section 20 forward or backward or the like while checking the moving image 38 displayed on the display apparatus 13. When he/she finds a lesion or the like in an observed area, he/she operates the still image capturing instruction unit 32 to capture a still image of the observed area, and performs diagnosis and treatment such as biopsy. Similarly, the moving image 38 and the still image 39 are displayed on the display unit 16 that is connected to the medical information processing apparatus 14 (a processor, a medical information processing apparatus) described below. In a case where the moving image 38 and the still image 39 are displayed on the display unit 16, reporting display is also performed. Thus, it is preferable that the user make a diagnosis or the like by viewing the display on the display unit 16.

Medical Information Processing Apparatus

Figure 4:
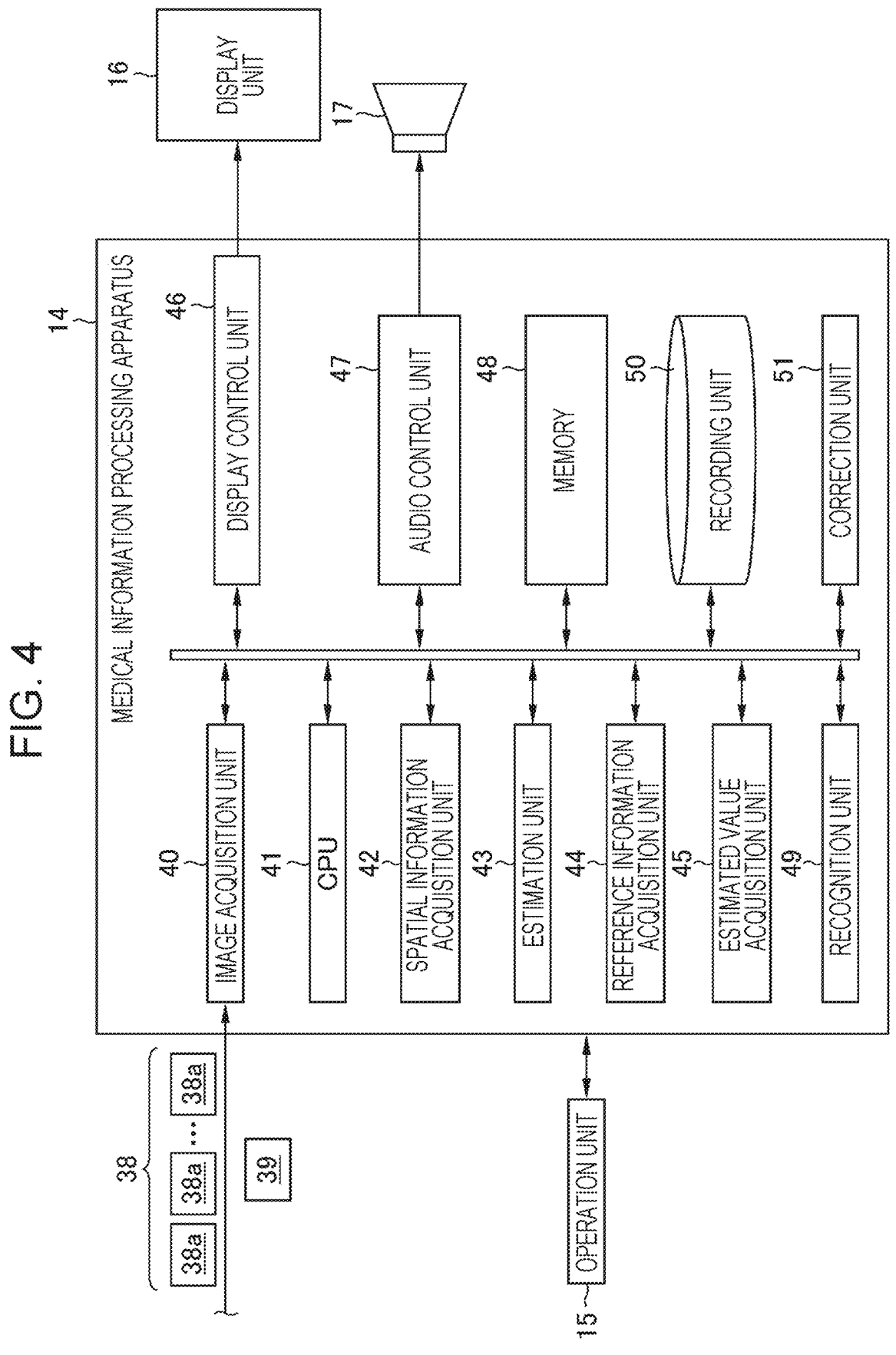
FIG. 4 is a block diagram illustrating an embodiment of a medical information processing apparatus.

FIG. 4 is a block diagram illustrating the configuration of the medical information processing apparatus 14. The medical information processing apparatus 14 sequentially acquires time-series endoscopic images and causes the display unit 16 to display the endoscopic images and medical information about a lumen (spatial information, a three-dimensional environment map, the distal end position of the endoscope, or the like). The medical information processing apparatus 14 is constituted by, for example, a computer. The operation unit 15 includes buttons provided in the handheld operation section 21 of the endoscope 10, in addition to a keyboard, a mouse, and the like that are connected to the computer in a wired manner or a wireless manner. Various types of monitors, such as a liquid crystal monitor, connectable to the computer may be used as the display unit 16.

The medical information processing apparatus 14 is constituted by an image acquisition unit 40, a central processing unit (CPU) 41, a spatial information acquisition unit 42, an estimation unit 43, a reference information acquisition unit 44, an estimated value acquisition unit 45, a display control unit 46, an audio control unit 47, a memory 48, a recognition unit 49, a recording unit 50, and a correction unit 51.

The CPU 41 operates on the basis of various programs including an operating system and a medical information processing program stored in the memory 48, centrally controls individual components of the medical information processing apparatus 14, and functions as a part of these components.

The image acquisition unit 40 sequentially acquires time-series endoscopic images (an image acquisition process). The image acquisition unit 40 acquires time-series endoscopic images including a photographic subject image from the endoscope processor apparatus 12 (FIG. 3) by using an image input/output interface that is not illustrated and that is connected to the endoscope processor apparatus 12 in a wired manner or a wireless manner. In this example, the moving image 38 captured by the endoscope 10 is acquired. In a case where the above-described still image 39 is captured during capturing of the moving image 38 by the endoscope 10, the image acquisition unit 40 acquires the moving image 38 and the still image 39 from the endoscope processor apparatus 12. In this example, a description will be given by using the intraluminal image P (FIG. 1A) of a large intestine as an example of an endoscopic image.

The spatial information acquisition unit 42 sequentially acquires pieces of spatial information (depth information, depth map) of a lumen on the basis of the endoscopic images, and the estimation unit 43 estimates, on the basis of the acquired pieces of spatial information, at least one of a three-dimensional environment map of the lumen or the distal end position of the endoscope. The reference information acquisition unit 44 acquires reference information about the shape and/or absolute size of the lumen, and the estimated value acquisition unit 45 acquires, from the spatial information and/or the three-dimensional environment map, an estimated value to be compared with the reference information. The correction unit 51 corrects one or more of the spatial information, the three-dimensional environment map, and the distal end position of the endoscope by using the reference information. The display control unit 46 generates image data to be displayed on the basis of the endoscopic images (the moving image 38) acquired by the image acquisition unit 40 and outputs the image data to the display unit 16 (a display apparatus). In addition, the display control unit 46 outputs an estimated value of medical information, reference information, a corrected value, a recognition result of a region of interest, and the like to the display unit 16. The audio control unit 47 controls a sound to be output from a speaker 17 (for example, a reporting sound to a user). The recognition unit 49 recognizes (for example, detects or classifies) a region of interest from an endoscopic image. The correction unit 51 corrects one or more of the spatial information, the three-dimensional environment map, and the distal end position of the endoscope by using the reference information.

The functions of the above-described components of the medical information processing apparatus 14 can be implemented by various types of processors. The various types of processors include a central processing unit (CPU), which is a general-purpose processor that executes software (program) and functions as various processing units; a programmable logic device (PLD), which is a processor whose circuit configuration is changeable after manufacturing, such as a field programmable gate array (FPGA); a dedicated electric circuit, which is a processor having a circuit configuration designed specifically for performing specific processing, such as an application specific integrated circuit (ASIC); and the like.

A single processing unit may be constituted by one of these various types of processors or may be constituted by two or more processors of the same type or different types (for example, a combination of a plurality of FPGAs or a combination of a CPU and an FPGA). A plurality of processing units may be constituted by a single processor. Examples in which a plurality of processing units are constitute by a single processor are as follows. Firstly, as represented by a computer such as a client or a server, a combination of one or more CPUs and software constitute one processor, and the processor functions as a plurality of processing units. Secondly, as represented by a system on chip (SoC) or the like, a processor in which a single integrated circuit (IC) chip implements the function of an entire system including a plurality of processing units is used. In this way, each component of the medical information processing apparatus 14 can be constituted as a hardware structure by using one or more of the above-described various types of processors.

Furthermore, the hardware structure of these processors is, more specifically, electric circuitry including a combination of circuit elements, such as semiconductor elements. Hereinafter, a description will be given of an example of a layer configuration in a case where the recognition unit 49 is constituted by a CNN. The CNN includes an input layer, an intermediate layer, and an output layer. The input layer receives an endoscopic image acquired by the image acquisition unit 40 and outputs a feature quantity. The intermediate layer includes convolutional layers and pooling layers, and receives the feature quantity output from the input layer and calculates another feature quantity. These layers each have a structure in which a plurality of "nodes" are connected by "edges" and hold a plurality of weight parameters. The values of the weight parameters change as learning progresses. The output layer recognizes a region of interest in an input medical image on the basis of the feature quantity output from the intermediate layer and outputs the result thereof.

In this example, upon sequentially receiving time-series endoscopic images, the recognition unit 49 recognizes (detects) the position of a region of interest in each of the received medical images, outputs information about the position (position information), recognizes (classifies) the class to which the region of interest belongs among a plurality of classes, and outputs information indicating the recognized class (class information, type information).

In the aspect illustrated in FIGS. 3 and 4, the endoscope processor apparatus 12 generates an endoscopic image, and the medical information processing apparatus 14 performs processing based on the generated endoscopic image (acquisition of spatial information and so forth). However, the present invention is not limited to such an aspect, and the endoscope processor apparatus 12 may have some or all of the functions of the medical information processing apparatus 14. In this case, the endoscope processor apparatus 12 executes a process of acquiring spatial information and so forth.

The memory 48 includes a flash memory, a read-only memory (ROM), a random access memory (RAM), and the like. The flash memory or the ROM is a nonvolatile memory (a non-transitory recording medium) that stores computer-readable code or the like of programs, such as an operating system and the medical information processing program according to the present invention. The RAM is a volatile memory that is capable of high-speed data reading and writing and that functions as an area for temporarily storing various programs stored in the nonvolatile memory and as a work area for the CPU 41.

Figure 5:
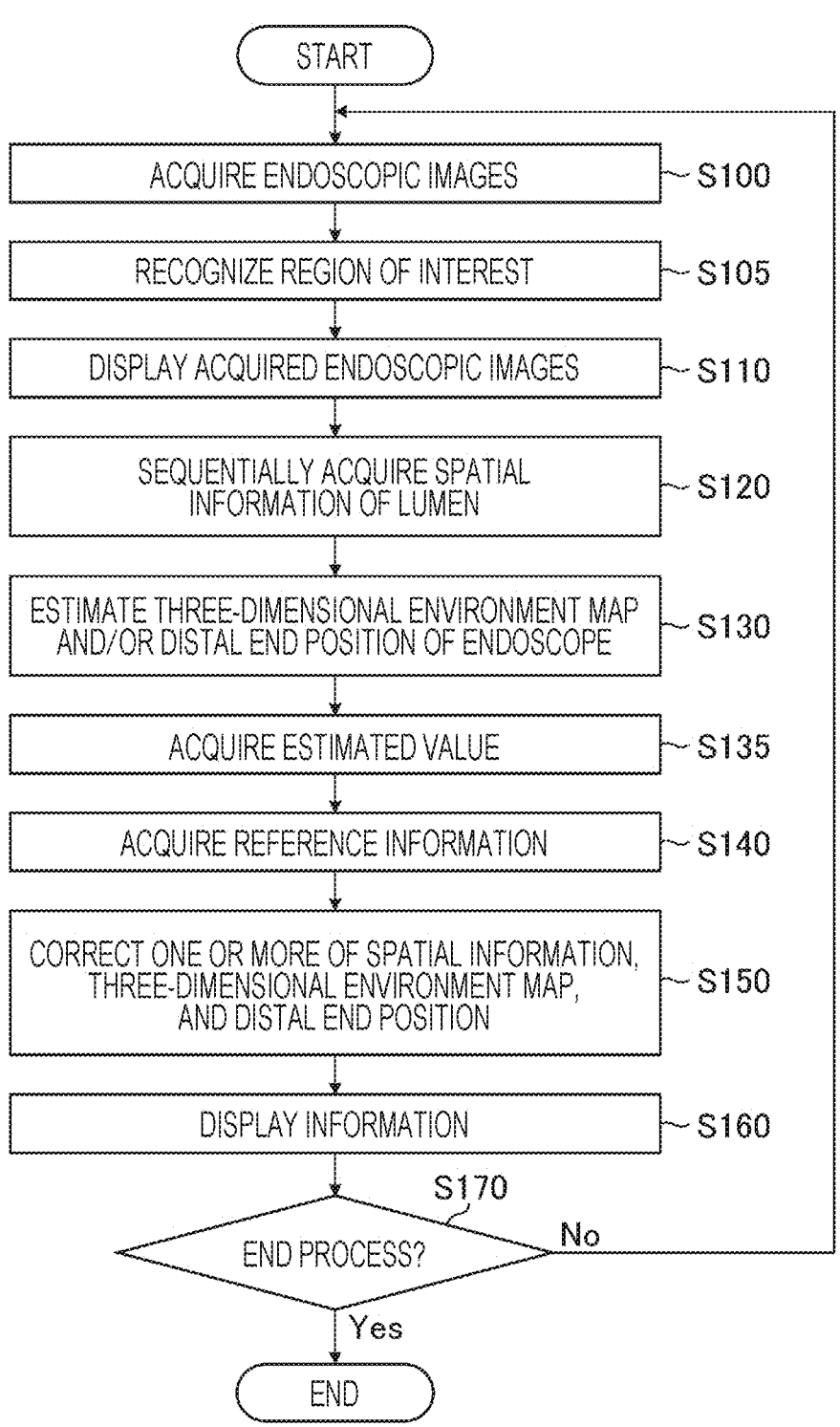
FIG. 5 is a flowchart illustrating a process of a medical information processing method.

The recording unit 50 is constituted by a hard disk device, a magneto-optical recording device, or the like, and stores an endoscopic image (the moving image 38, the still image 39), an estimated value and a corrected value of medical information (spatial information, a three-dimensional environment map, the distal end position of the endoscope 10, or the like), reference information about the shape and/or absolute size of a lumen, and so forth in association with each other.
Medical Information Processing Method and Medical Information Processing Program A medical information processing method using the medical information processing apparatus 14, and a program for causing the medical information processing apparatus 14 to execute the medical information processing method will be described. FIG. 5 is a flowchart illustrating a procedure of the medical information processing method according to the first embodiment of the present invention. The process described below may be executed in different order as necessary.
Acquisition of Endoscopic Images and Recognition of Region of Interest Upon the process being started, the image acquisition unit 40 (a processor) sequentially acquires endoscopic images via the endoscope 10 (step S100: an image acquisition process, an image acquisition step), and the recognition unit 49 recognizes a region of interest from the acquired endoscopic images (step S105: a recognition process, a recognition step). The recognition unit 49 may recognize a tool (an object having a known size) protruding from the endoscope 10 as a region of interest (a photographic subject), and may acquire an actually measured value of the size of a lumen on the basis of the recognition result (this aspect will be described below).

The display control unit 46 (a processor) causes the display apparatus 13 (a display apparatus) and the display unit 16 (a display apparatus) to display the acquired endoscopic images (step S110: a display control process, a display control step). In a case where a region of interest is recognized, the display control unit 46 causes the recognition result to be displayed (one aspect of reporting) (step S110: a display control process, a display control step). The display control unit 46 is capable of displaying the recognition result (a result of detection, classification, or the like) by displaying, for example, a figure, a symbol, a character, or the like in association with the position of the region of interest. In addition, the audio control unit 47 (a processor) may perform reporting by using a sound via the speaker 17.
Acquisition of Spatial Information, and Estimation of Three-Dimensional Environment Map and/or Self-Position The spatial information acquisition unit 42 (a processor) sequentially acquires pieces of spatial information (depth information, depth map) of the lumen on the basis of the sequentially acquired endoscopic images (step S120: a spatial information acquisition process, a spatial information acquisition step), and the estimation unit 43 (a processor) estimates a three-dimensional environment map and/or the distal end position of the endoscope on the basis of the acquired pieces of spatial information (step S130: an estimation process, an estimation step). The spatial information acquisition unit 42 is capable of acquiring spatial information from one endoscopic image, and is also capable of acquiring spatial information by using a plurality of endoscopic images that are different in imaging position. The spatial information acquisition unit 42 may acquire spatial information by using an estimator constituted through machine learning such as deep learning, or may acquire spatial information by using the technique described in the above-mentioned paper ("Detecting Deficient Coverage in Colonoscopies"). The spatial information acquisition unit 42 and the estimation unit 43 may calculate a score indicating the reliability of a processing result.

In the process in steps S120 and S130 (acquisition of spatial information, estimation of a three-dimensional environment map and/or the distal end position of the endoscope), for example, depth information and the self position (the position of the endoscope in the three-dimensional environment map) can be simultaneously estimated by, for example, simultaneous localization and mapping (SLAM). Such a technique is described in, for example, JP2020-156841A. Visual-SLAM based on image signals is described in "Andrew J. Davison, "Real-Time Simultaneous Localization and Mapping with a Single Camera", Proceedings of the 9th IEEE International Conference on Computer Vision Volume 2, 2003, pp. 1403-1410", JP2011-95797A, and so forth. SLAM using an output of an acceleration sensor or an inertial sensor may be used. IMU-SLAM (SLAM using an output of an inertial sensor) is described in, for example, JP2017-185254A.

The estimated value acquisition unit 45 (a processor) acquires an estimated value to be compared with reference information from the spatial information and/or the three-dimensional environment map (step S135: an estimated value acquisition process, an estimated value acquisition step). That is, the estimated value acquisition unit 45 designates (determines) a position at which an estimated value is to be acquired, and acquires an estimated value at the position. The estimated value acquisition unit 45 may acquire an estimated value for either or both of the spatial information and the three-dimensional environment map.

The estimated value acquisition unit 45 is capable of acquiring an estimated value at a designated position in a lumen. The estimated value acquisition unit 45 may designate a position at which an estimated value is to be acquired on the basis of a user operation or not on the basis of a user operation. In the case of designating a position on the basis of a user operation, for example, the user checks the result of a displayed depth map or three-dimensional environment map and performs an operation of designating a position for which estimation is considered inappropriate, and the estimation unit 43 is capable of acquiring an estimated value at the position designated by the operation. In the case of designating a position not on the basis of a user operation, the estimated value acquisition unit 45 is capable of designating, in an endoscopic image, a position at which a landmark is present, a position at which a tool or the like is present, a position at which the reliability of an estimation result is low, a position at which a change in shape or size is large, or the like, and acquiring an estimated value at the position. The estimated value acquisition unit 45 may designate a plurality of points for one endoscopic image and may acquire estimated values for the plurality of points.

Acquisition of Reference Information

The reference information acquisition unit 44 (a processor) acquires reference information about the shape and/or absolute size of a lumen (step S140: a reference information acquisition process, a reference information acquisition step).

Example of Reference Information

The reference information acquisition unit 44 is capable of acquiring, as "reference information", a numerical value indicating a standard shape and/or absolute size of a lumen. The "standard shape and/or absolute size of a lumen" may be actual data or may be a numerical value obtained by statistically processing actual data (for example, an average value, an average value±standard deviation, or the like). In the statistical processing, processing may be performed with classification by a condition such as age or sex.

The reference information acquisition unit 44 is also capable of acquiring a predetermined actually measured value as reference information. The "actually measured value" is, for example, a value calculated in advance on the basis of a medical image captured by a medical imaging capturing apparatus. Specifically, the reference information acquisition unit 44 is capable of acquiring, as an "actually measured value", a value calculated from a medical image captured by a CT apparatus, an MM apparatus, an X-ray imaging apparatus, or the like.

The recognition unit 49 may recognize, as a photographic subject, an object having a known size in an endoscopic image, and the reference information acquisition unit 44 may acquire, as an actually measured value, the size of a lumen at the position at which the photographic subject is present. In this case, the recognition unit 49 is capable of regarding a tool protruding from the distal end of the endoscope 10 as an "object having a known size" (it is assumed that the size of the tool is measured in advance and recorded in the recording unit 50 or the like). FIGS. 6A and 6B are tables illustrating examples of actually measured values of tools.

Figure 7:
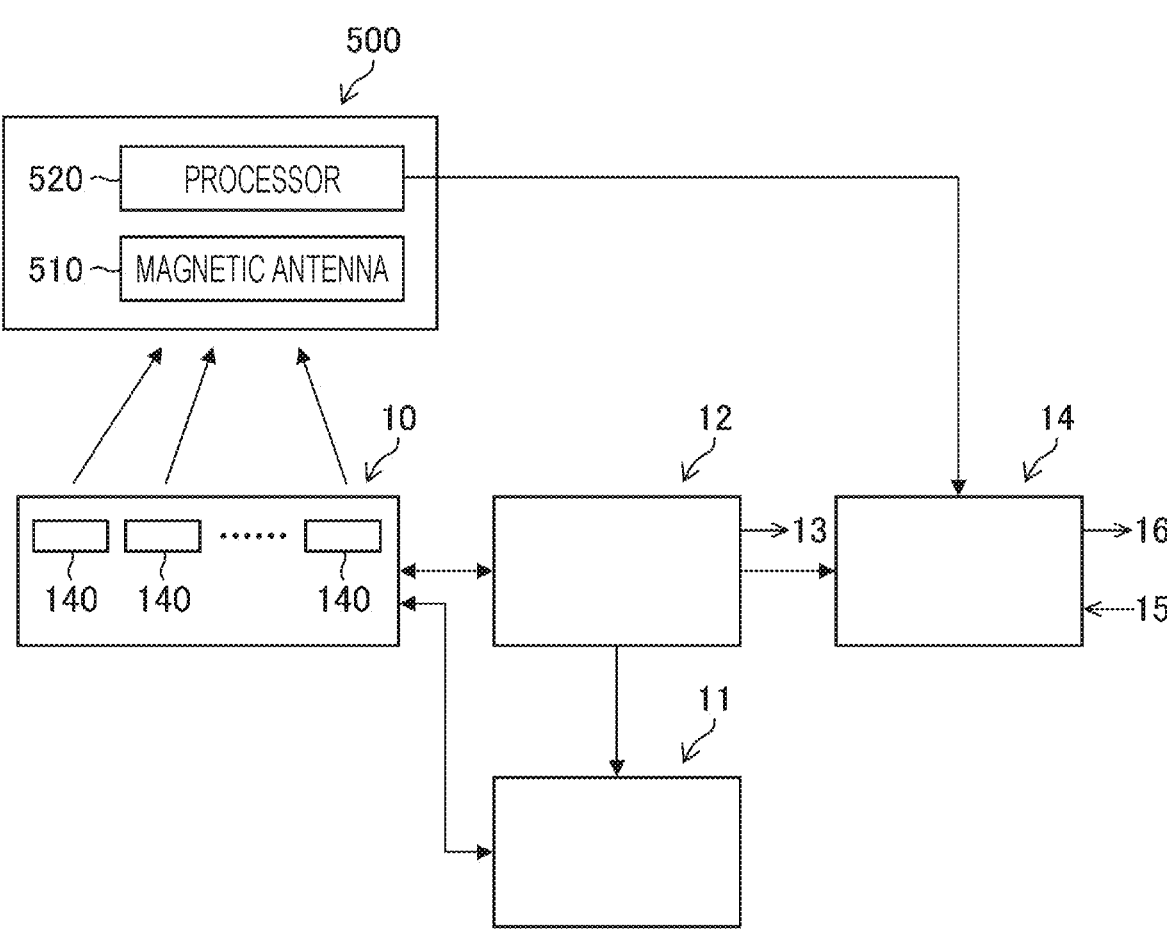
FIG. 7 is a diagram illustrating a state of measurement using an endoscope shape measurement apparatus.

The reference information acquisition unit 44 may acquire an actually measured value by using a measurement apparatus connected to the medical information processing apparatus 14 (a medical information processing apparatus). FIG. 7 is a diagram illustrating a state in which an endoscope shape measurement apparatus 500 (a measurement apparatus) is connected to the medical information processing apparatus 14. In the example illustrated in FIG. 7, a plurality of magnetism generators 140 (magnets, coils, or the like) that generate magnetism are provided in the endoscope 10, and the endoscope shape measurement apparatus 500 detects the magnetism generated by the magnetism generators 140 by using a magnetic antenna 510. The reference information acquisition unit 44 calculates the position and/or shape of the endoscope 10 on the basis of the detection result, and calculates an "actually measured value" (the shape and/or absolute size of a lumen) on the basis of the result.

Alternatively, laser light may be radiated from the distal end part of the endoscope and the reference information acquisition unit 44 may acquire an actually measured value (the shape and/or size of a lumen) on the basis of a pattern formed in the subject by the laser light. Measurement using patterned laser light in an endoscope system is described in, for example, JP2017-86803A.

Correction of Acquired or Estimated Information

The correction unit 51 (a processor) corrects one or more of the spatial information, the three-dimensional environment map, and the distal end position of the endoscope by using the estimated value acquired in step S135 and the reference information acquired in step S140 (step S150: a correction process, a correction step).

Figure 8A:
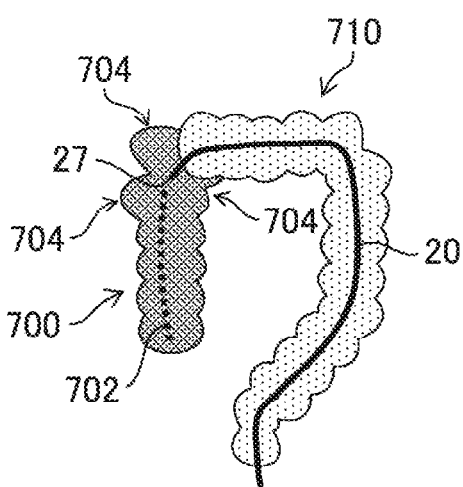
FIGS. 8A and 8B are diagrams illustrating a state of correcting an estimated value on the basis of reference information.
Figure 8B:
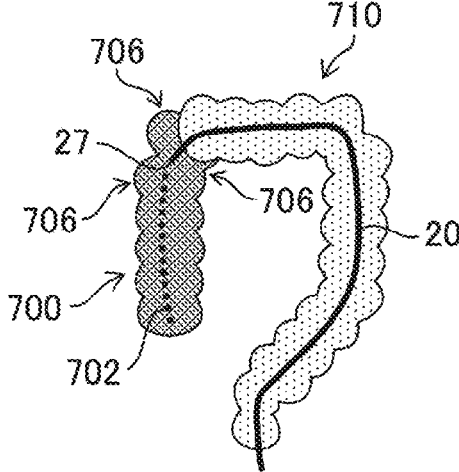

FIGS. 8A and 8B are conceptual diagrams illustrating an example of correction. For example, when it is estimated that "the diameter of the large intestine is 15 cm" in the region 704 illustrated in FIG. 8A, the correction unit 51 is capable of determining that "a standard diameter of the lumen is about 8 cm (an example of reference information), and thus the estimation result is too large as compared with this numerical value". Accordingly, as illustrated in FIG. 8B, the correction unit 51 is capable of correcting the diameter of the portion in which an estimation error occurs to 8 cm, which is the "standard diameter of the lumen". The state after the correction is a region 706.

In a case where the estimated value is larger than the reference information due to an estimation error, the correction unit 51 need not necessarily cause the estimated value to completely match the reference information in correction, and only needs to cause the estimated value (15 cm in the above-described example) to approach the reference information (8 cm in the above-described example). In a case where a problem occurs, for example, "if the estimated value is caused to completely match the reference information by correction, discontinuity with the size in the vicinity occurs", the correction unit 51 is capable of using an intermediate value between the estimated value and the reference information as a corrected value (for example, in a case where the diameter in the vicinity is 9 cm in the above-described example, 9 cm, which is the middle between 15 cm and 8 cm, can be used as a corrected value).

Figures 9A, 9B:
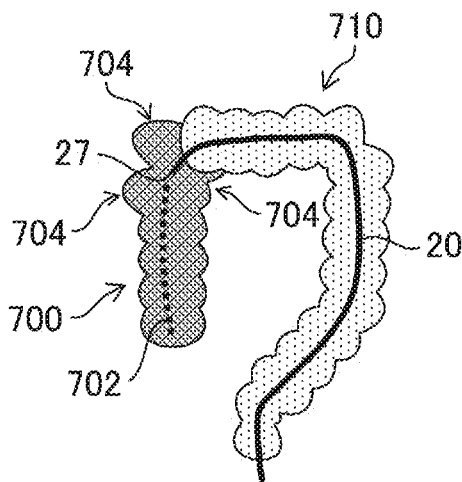
FIGS. 9A and 9B are diagrams illustrating a state of correcting an estimated value through comparison with an object having a known size.

FIGS. 9A and 9B are conceptual diagrams illustrating another example of correction (correction using a tool having a known size). FIG. 9A illustrates a state in which an estimation error occurs in the region 704 as in FIG. 8A. FIG. 9B illustrates a state in which a tool 620 is seen in an endoscopic image 600 in the region 704 (a state in which the recognition unit 49 has recognized the tool 620 as a photographic subject in the endoscopic image 600). It is assumed that the size of the tool 620 is known.

In this situation, the estimated value acquisition unit 45 (a processor) acquires, from the spatial information and/or the three-dimensional environment map, an estimated value of the size of a fold 610 of the lumen at the position at which the tool 620 is present (an example of a "position designated in the lumen") (an estimated value acquisition process, an estimated value acquisition step).

The reference information acquisition unit 44 (a processor) acquires, for example, the size of the tool 620 (an example of a "predetermined actually measured value") illustrated in the tables in FIGS. 6A and 6B as "reference information" (a reference information acquisition process, a reference information acquisition step). For example, it is assumed that the estimated value of a diameter D1 of the fold 610 is 8 cm and the diameter D2 of the tool 620 is 1 cm.

In this case, the correction unit 51 is capable of correcting the diameter D1 to, for example, "4 cm" by comparing the diameter of the fold 610 in the endoscopic image 600 with the value of the diameter D2 of the tool 620 (a correction process, a correction step).

In correction, a technique "Pose Graph Optimization", which is often used in SLAM, such as Oriented FAST and Rotated Brief SLAM (ORB-SLAM) or Large-Scale Direct Monocular SLAM (LSD-SLAM), can be used. In Pose Graph Optimization, when information serving as a trigger for correction (for example, deviation information of a position when a loop is found, which is called Loop Closure) is acquired during position estimation and map construction using SLAM, position estimation or a map for acquiring the trigger is corrected on the basis of the information. In a case where Pose Graph Optimization is applied to the first embodiment, correction can be performed using, as a trigger, acquisition of reference information. The details of such Pose Graph Optimization are also described in Rainer Kuemmerle et al, "g2o: A General Framework for Graph Optimization", http://ais.informatik.uni-freiburg.de/publications/papers/kuemmerle11icra.pdf).

In the correction of the estimated value, the correction unit 51 may select a method to be used for the correction from among a plurality of methods, or may combine a plurality of methods. In addition, the correction unit 51 may determine, in accordance with a user operation, which method is to be used to perform correction.

Display of Result

The display control unit 46 (a processor) causes the display unit 16 (a display apparatus) to display information such as the space information, the three-dimensional environment map, and the distal end map (step S160: an information display process, an information display step). The information caused to be displayed by the display control unit 46 may be a value before correction or a value after correction. Both may be compared and displayed. The display control unit 46 may determine, in accordance with a user operation, which information is to be displayed. In addition, the display control unit 46 may sequentially update display in parallel with sequential capturing/acquisition of endoscopic images in accordance with an insertion/removal operation of the endoscope.

The medical information processing apparatus 14 repeats the above-described process until YES is obtained in step S170.

As described above, according to the first embodiment of the present invention, one or more of pieces of acquired or estimated medical information (spatial information, a three-dimensional environment map, and the distal end position of the endoscope) are corrected by using reference information, and thus accurate medical information can be acquired.

Although the case of observing a large intestine has been described in the first embodiment, the present invention is also applicable to the case of observing a lumen of an esophagus, stomach, or the like.

The examples of the present invention have been described above. The present invention is not limited to the above-described embodiment, and various modifications can be made without departing from the gist of the present invention.

REFERENCE SIGNS LIST

9 endoscope system
10 endoscope
11 light source apparatus
12 endoscope processor apparatus
13 display apparatus
14 medical information processing apparatus
15 operation unit
16 display unit
17 speaker
20 insertion section
21 handheld operation section
22 universal cord
25 soft part
26 bending part
27 distal end part
28 imaging element
29 bending operation knob
30 air/water supply button
31 suction button
32 still image capturing instruction unit
33 treatment tool introduction port
34 graduations
35 light guide
36 signal cable
37*a* connector
37*b* connector
38 moving image
38*a* frame image
39 still image
40 image acquisition unit
41 CPU
42 spatial information acquisition unit
43 estimation unit
44 reference information acquisition unit
45 estimated value acquisition unit
46 display control unit
47 audio control unit
48 memory
49 recognition unit
50 recording unit
51 correction unit
140 magnetism generator
500 endoscope shape measurement apparatus
510 magnetic antenna
600 endoscopic image
620 tool
700 depth map
702 dotted line
704 region
706 region
710 large intestine
D1 diameter
D2 diameter I depth image P intraluminal image S100 to S170 individual steps of medical information processing method

What is claimed is:

1. A medical information processing apparatus comprising a processor, the processor being configured to execute:

a spatial information acquisition process of sequentially acquiring pieces of spatial information of a lumen on the basis of endoscopic images sequentially acquired by an endoscope;

an estimation process of estimating, on the basis of the pieces of spatial information sequentially acquired, at least one of a three-dimensional environment map of the lumen or a distal end position of the endoscope;

a reference information acquisition process of acquiring a predetermined actually measured value of the lumen as reference information; and a correction process of correcting, using the reference information, one or more of the spatial information, the three-dimensional environment map, and the distal end position of the endoscope.

2. The medical information processing apparatus according to claim 1, wherein the processor is configured to acquire the spatial information by using a plurality of endoscopic images that are different in imaging position.

3. The medical information processing apparatus according to claim 1, wherein the processor is configured to execute an estimated value acquisition process of acquiring, from the spatial information and/or the three-dimensional environment map, an estimated value to be compared with the reference information, and in the correction process, correct one or more of the spatial information, the three-dimensional environment map, and the distal end position of the endoscope to cause the estimated value to approach the reference information.

4. The medical information processing apparatus according to claim 3, wherein the processor is configured to, in the estimated value acquisition process, acquire the estimated value at a position designated in the lumen.

5. The medical information processing apparatus according to claim 4, wherein the processor is configured to in the spatial information acquisition process, sequentially acquire the endoscopic images via the endoscope, and in the estimated value acquisition process, designate the position on the basis of the acquired endoscopic images.

6. The medical information processing apparatus according to claim 1, wherein the processor is configured to, in the reference information acquisition process, further acquire, as the reference information, a numerical value indicating a standard size of the lumen.

7. The medical information processing apparatus according to claim 1, wherein the processor is configured to, in the reference information acquisition process, acquire, as the actually measured value, a value calculated in advance on the basis of a medical image captured by a medical image capturing apparatus.

8. The medical information processing apparatus according to claim 1, wherein the processor is configured to, in the reference information acquisition process, recognize a photographic subject in an endoscopic image acquired via the endoscope, and acquire the actually measured value on the basis of a result of the recognition.

9. The medical information processing apparatus according to claim 8, wherein the processor is configured to recognize, as the photographic subject, an object having a known size, and acquire, as the actually measured value, a size of the lumen at a location at which the photographic subject is present.

10. The medical information processing apparatus according to claim 8, wherein the processor is configured to recognize, as the photographic subject, a tool protruding from the endoscope.

11. The medical information processing apparatus according to claim 1, wherein the processor is configured to, in the reference information acquisition process, acquire the actually measured value by using a measurement apparatus connected to the medical information processing apparatus.

12. An endoscope system comprising:

the medical information processing apparatus according to claim 1; and an endoscope including an imaging unit configured to sequentially capture medical images of a subject.

13. A medical information processing method to be executed by a medical information processing apparatus including a processor, the medical information processing method comprising:

a spatial information acquisition step of sequentially acquiring pieces of spatial information of a lumen on the basis of endoscopic images sequentially acquired by an endoscope;

an estimation step of estimating, on the basis of the pieces of spatial information sequentially acquired, at least one of a three-dimensional environment map of the lumen or a distal end position of the endoscope;

a reference information acquisition step of acquiring a predetermined actually measured value of the lumen as reference information; and a correction step of correcting, using the reference information, one or more of the spatial information, the three-dimensional environment map, and the distal end position of the endoscope.

14. A non-transitory, computer-readable tangible recording medium which records thereon a program for causing, when read by a computer, the computer to execute the medical information processing method according to claim 13.

15. A medical information processing apparatus comprising a processor, the processor being configured to execute:

a spatial information acquisition process of sequentially acquiring pieces of spatial information of a lumen on the basis of endoscopic images sequentially acquired by an endoscope;

an estimation process of estimating, on the basis of the pieces of spatial information sequentially acquired, at least one of a three-dimensional environment map of the lumen or a distal end position of the endoscope;

a reference information acquisition process of acquiring reference information about a shape and/or an absolute size of the lumen;

an estimated value acquisition process of acquiring, from the spatial information and/or the three-dimensional environment map, an estimated value to be compared with the reference information; and a correction process of correcting, using the reference information, one or more of the spatial information, the three-dimensional environment map, and the distal end position of the endoscope to cause the estimated value to approach the reference information.

16. An endoscope system comprising:

the medical information processing apparatus according to claim 15; and an endoscope including an imaging unit configured to sequentially capture medical images of a subject.

17. A medical information processing method to be executed by a medical information processing apparatus including a processor, the medical information processing method comprising:

a spatial information acquisition process of sequentially acquiring pieces of spatial information of a lumen on the basis of endoscopic images sequentially acquired by an endoscope;

an estimation process of estimating, on the basis of the pieces of spatial information sequentially acquired, at least one of a three-dimensional environment map of the lumen or a distal end position of the endoscope;

a reference information acquisition process of acquiring reference information about a shape and/or an absolute size of the lumen;

an estimated value acquisition process of acquiring, from the spatial information and/or the three-dimensional environment map, an estimated value to be compared with the reference information; and a correction process of correcting, using the reference information, one or more of the spatial information, the three-dimensional environment map, and the distal end position of the endoscope to cause the estimated value to approach the reference information.

18. A non-transitory, computer-readable tangible recording medium which records thereon a program for causing, when read by a computer, the computer to execute the medical information processing method according to claim 17.

* * * * *